United States Patent [19]

Herrera

[11] Patent Number: Plant 7,233

[45] Date of Patent: May 22, 1990

[54] CHRYSANTHEMUM PLANT NAMED YELLOW COMET

[75] Inventor: Camilo Herrera, Bogota, Colombia

[73] Assignee: Whitefield Corporation, Panama

[21] Appl. No.: 337,425

[22] Filed: Apr. 13, 1989

[51] Int. Cl.[5] ..... A01H 5/00

[52] U.S. Cl. ..... Plt./78

[58] Field of Search ..... Plt./78

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Yellow Comet particularly characterized as to uniqueness by the combined characteristics of flat capitulum form; quilled capitulum type; yellow ray floret color; diameter across face of capitulum of up to 9 cm at maturity; uniform nine week photoperiodic flowering response to short days; medium plant height when grown single stem; 15 to 25 cm peduncles on open, normally terminal sprays; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Yellow Comet.

Yellow Comet is a spontaneous mutation of the cultivar Comet, disclosed in U.S. Plant Pat. No. 5,809, and was selected to expand the color range of the parental variety. Yellow Comet was discovered and selected as one flowering plant within a flowering block of Comet by Camilo Herrera in February of 1986, in a controlled environment at Jardines de los Andes, Madrid Cundinamarca, Colombia, South America.

The first act of asexual reproduction of Yellow Comet was accomplished when vegetative cuttings were taken from the initial selection in August of 1986 in a controlled environment at Jardines de los Andes, Madrid Cundinamarca, Colombia, South America, by technicians working under formulations established and supervised by Camilo Herrera.

Horticultural examination of controlled flowerings of successive plantings has shown that the unique combination of characteristics as herein disclosed for Yellow Comet are firmly fixed and are retained through successive generations of asexual reproduction.

Yellow Comet has not been observed under all possible environmental conditions. The phenotype may vary significantly with variations in environment such as temperature, light intensity and daylength.

The following observations, measurements and comparisons describe plants grown at Jardines de los Andes, Madrid Cundinamarca, Colombia, South America, under greenhouse conditions which approximate those generally used in commercial greenhouse practice. Flowering plant material was sent from Colombia, South America to Salinas, Calif., for observations, measurements and color readings.

The following traits have been repeatedly observed and are determined to be basic characteristics of Yellow Comet, which, in combination, distinguish this Chrysanthemum as a new and distinct cultivar;

1. Flat capitulum form.
2. Quilled capitulum type.
3. Yellow ray floret color.
4. Diameter across face of capitulum up to 9 cm at maturity.

5. Uniform nine week photoperiodic flowering response to short days.
6. Peduncle length ranging from 15 to 25 cm.
7. Medium plant height, requiring two long day weeks prior to short days to attain a flowered plant height of 90 to 100 cm for year-round flowerings when grown single stem.
8. Excellent tolerance to low temperatures for bud initiation and flower development.

The accompanying photographic drawings show typical inflorescence and leaf characteristics of Yellow Comet, with the colors being as nearly true as possible with illustrations of this type.

Sheet 1 is a color photograph of Yellow Comet grown as a single stem cut spray.

Sheet 2 is a black and white photograph of three views of the inflorescence of Yellow Comet.

Sheet 3 is a black and white photograph showing the supper and under sides of the leaves of Yellow Comet at three stages of development (mature, intermediate and immature).

Of the commercial cultivars known to the inventor, the most similar in comparison to Yellow Comet is the parent cultivar Comet. All traits of Yellow Comet are similar to those of Comet, except the color of the ray florets. The color of the ray florets of Yellow Comet is yellow, while the color of Comet is described as purple.

In the following description color references are made to The Royal Horticultural Society Colour Chart. The color values were determined in Salinas, Calif. on Oct. 14, 1988.

Classification

*Botanical.*—*Dendranthema grandiflora* cv Yellow Comet.

*Commercial.*—Quilled cut spray mum.

INFLORESCENCE

A. Capitulum:

*Form.*—Flat.

*Type.*—Quilled.

*Diameter across face.*—Up to 9 cm at maturity.

B. Corolla of ray florets:

*Color (general tonality from a distance of three meters).*—Yellow.

*Color (inner surface of tubular rays).*—6B.

*Color* (*outer surface of tubular rays*).—6B to 6C.

*Shape.*—Straight, concave, pointed.

C. Corolla of disc florets:

*Color* (*mature*).—1B.

*Color* (*immature*).—145A. Few disc florets. Number of disc florets depending on environmental conditions.

D. Reproductive organs:

*Androecium.*—Present on disc florets only.

*Gynoecium.*—Present on both ray and disc florets.

PLANT

A. General appearance:

*Height.*—Medium; 90 to 100 cm as a single stem cut mum with fourteen long days prior to short days.

B. Foliage:

*Color* (*upper surface*).—137A.

*Color* (*under surface*).—148B.

*Shape.*—Deeply lobed and serrated.

I claim:

1. A new and distinct Chrysanthemum plant named Yellow Comet, as described and illustrated.

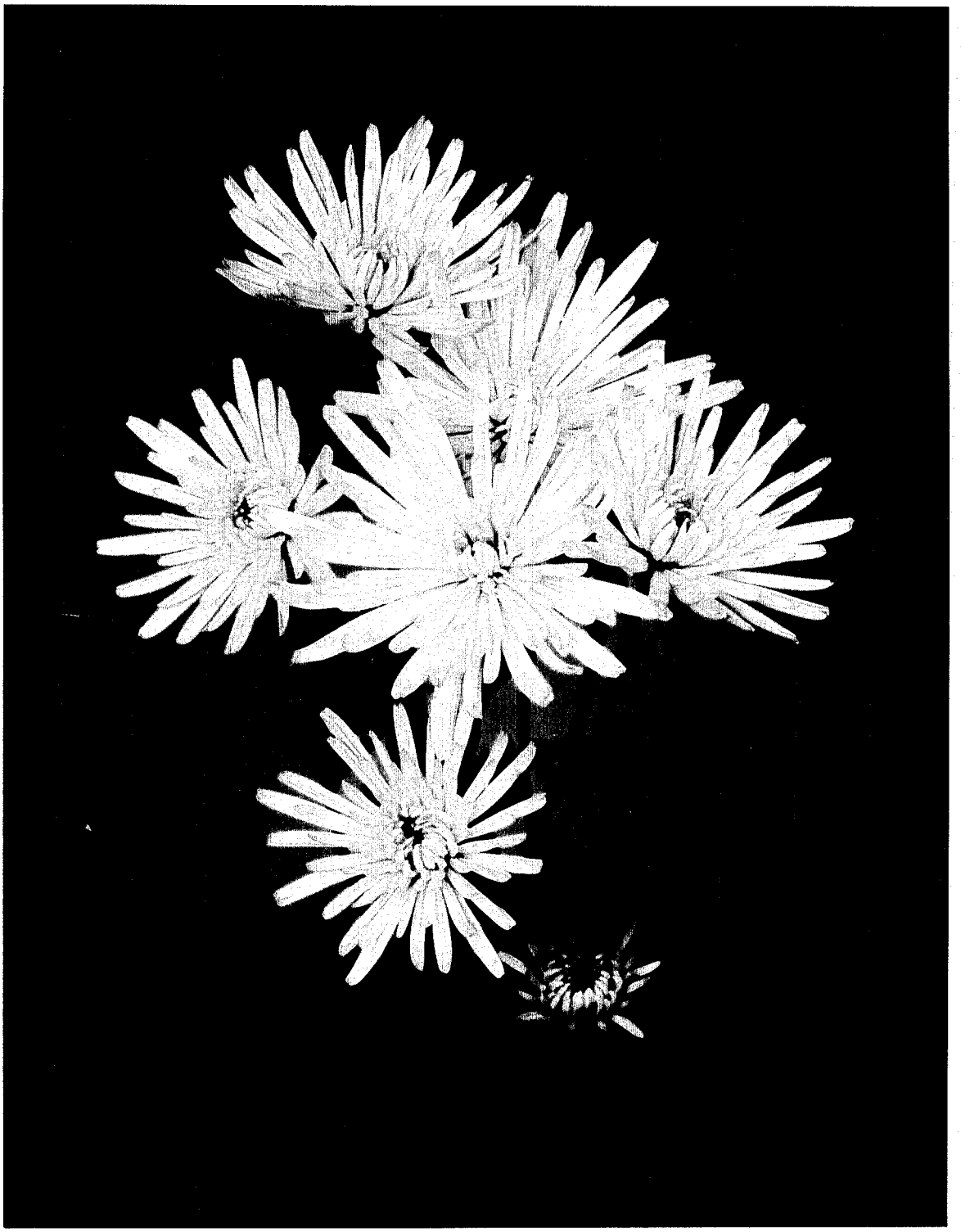

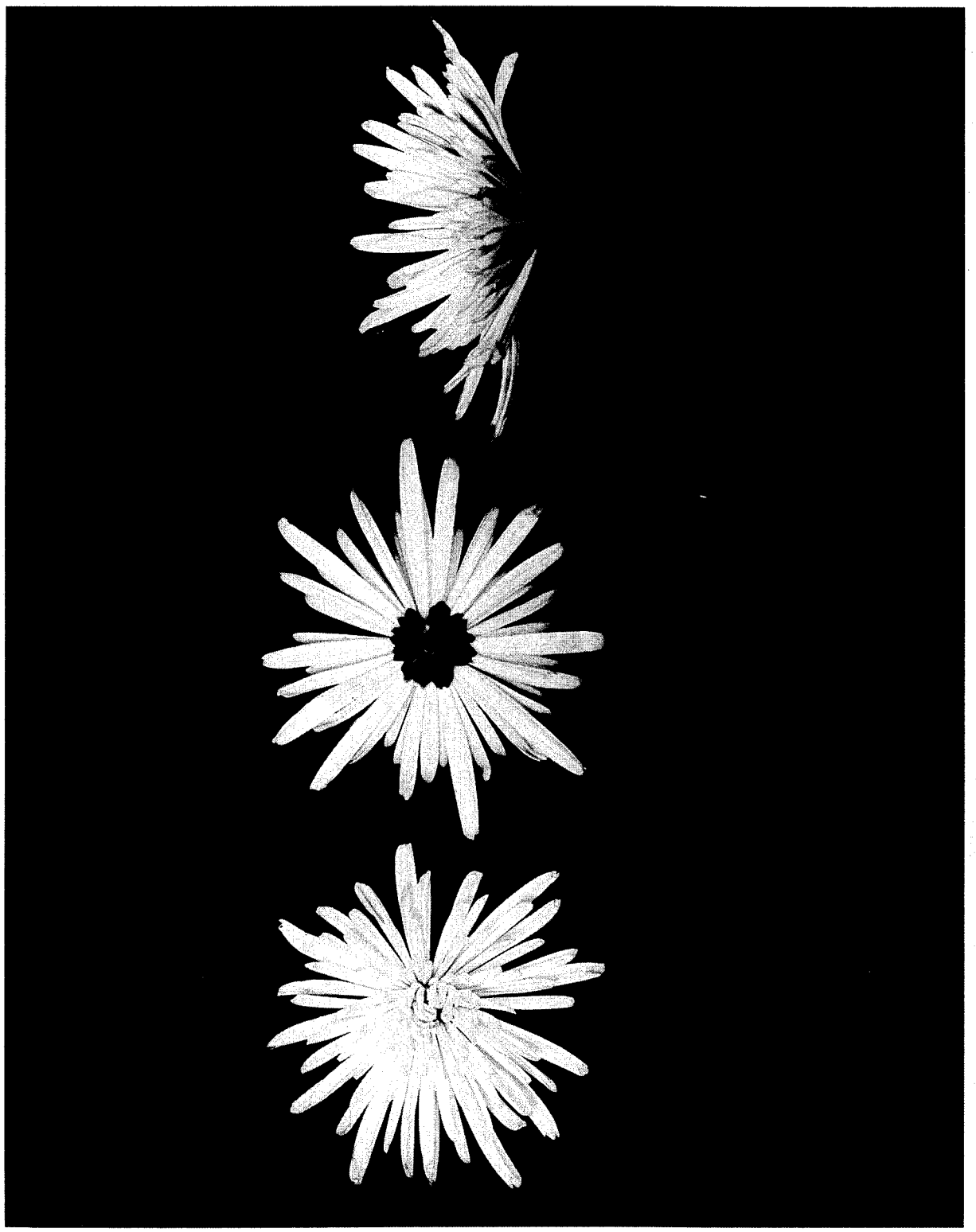

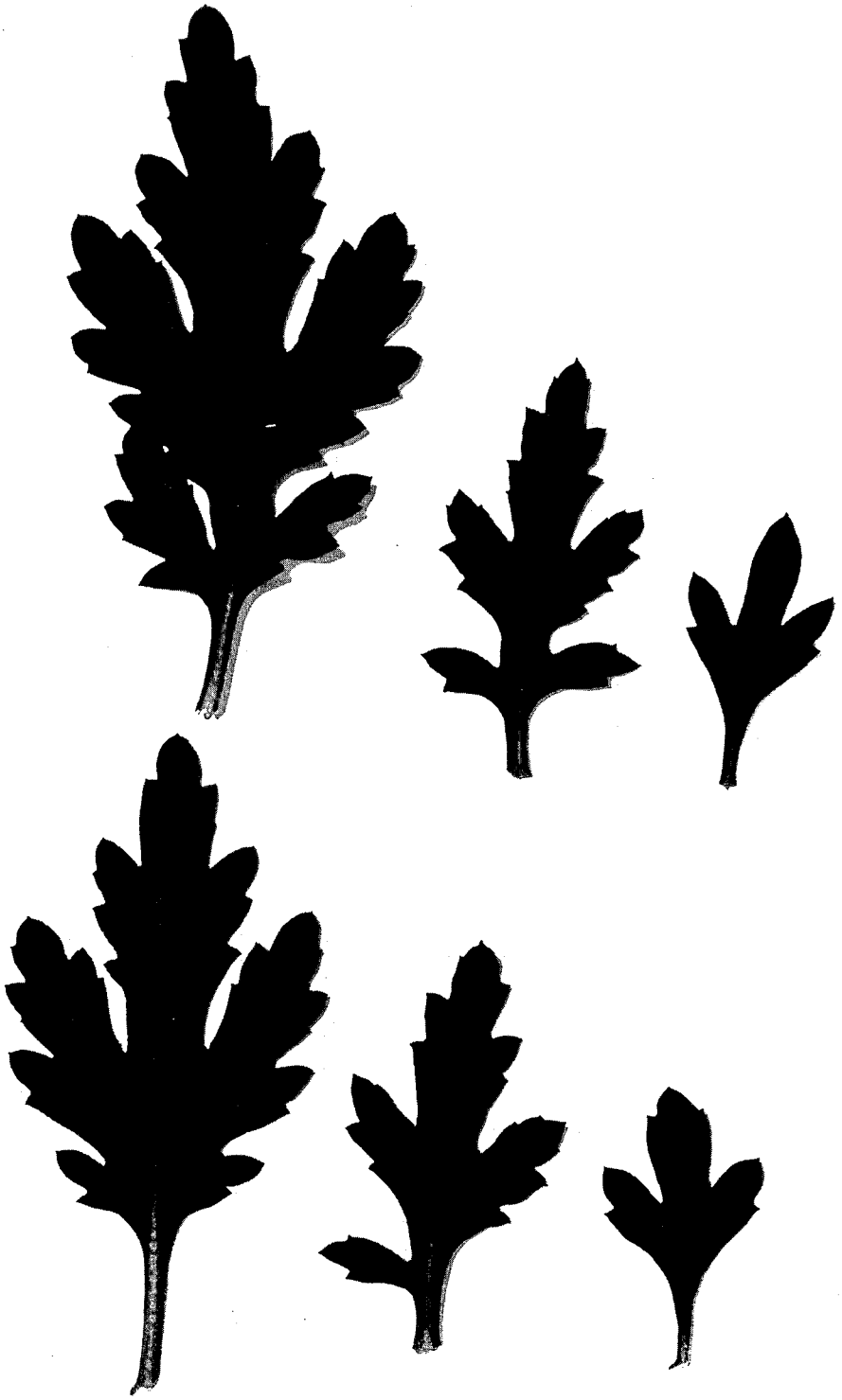

* * * * *